Figure 1:
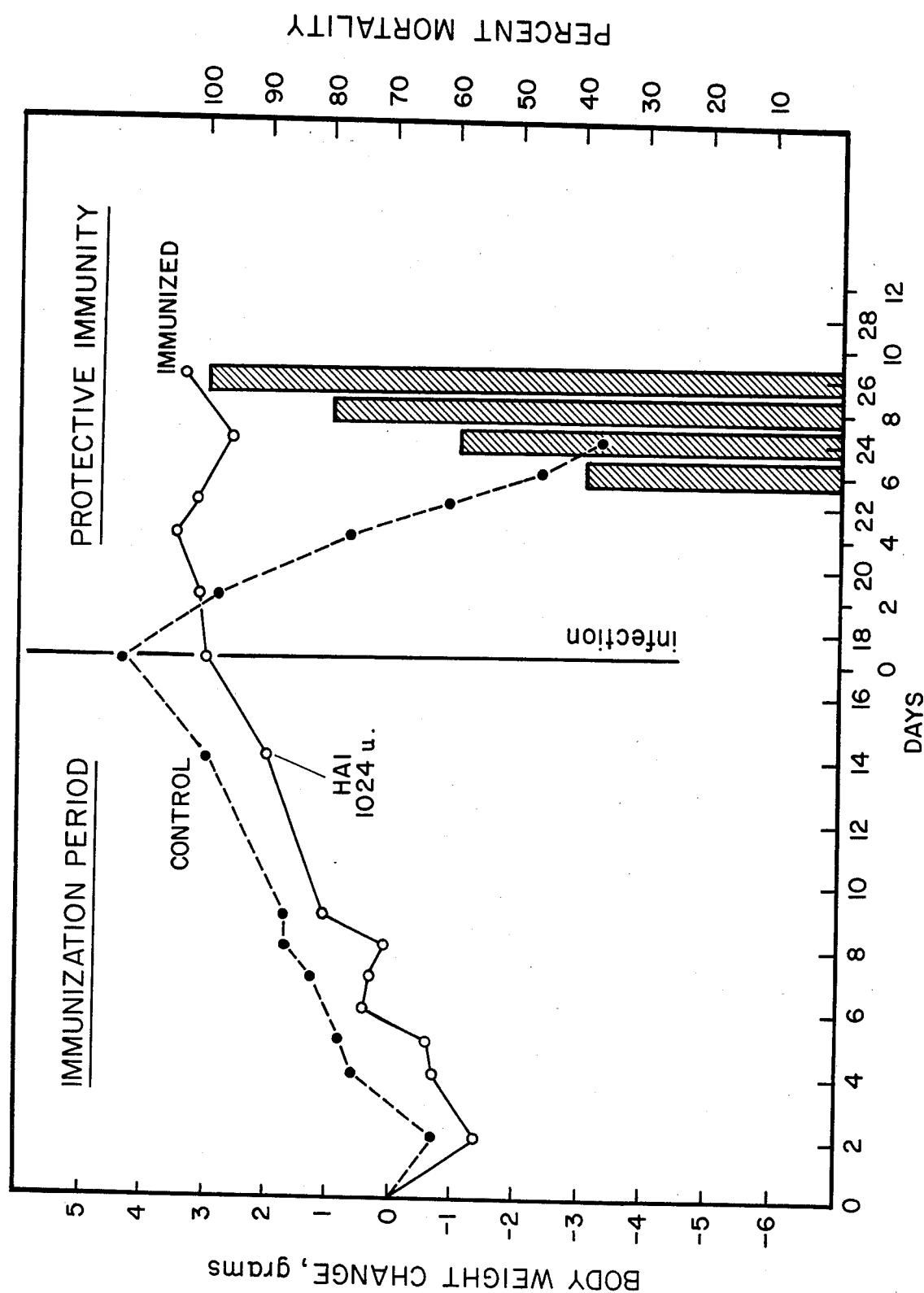

United States Patent [19]

Gabliks

[11] Patent Number: 4,783,411

[45] Date of Patent: Nov. 8, 1988

[54] INFLUENZA-A VIRUS VACCINE FROM FISH CELL CULTURES

[76] Inventor: Janis Gabliks, 103 Cabot St., Newton, Mass. 02158

[21] Appl. No.: 663,322

[22] Filed: Oct. 22, 1984

[51] Int. Cl.[4] ..................... C12N 7/08; A61K 39/145

[52] U.S. Cl. ..................................... 435/237; 424/89; 435/240.2

[58] Field of Search ............................ 424/89, 93, 88; 435/240, 241, 235-239, 240.2

[56] References Cited

U.S. PATENT DOCUMENTS

| | | | |
|---|---|---|---|
| 3,950,511 | 4/1976 | Gaudry | 424/89 |
| 3,953,592 | 4/1976 | Peetermans | 424/89 |
| 3,991,179 | 11/1976 | Beare | 424/89 |
| 4,219,543 | 8/1980 | Hartmann | 424/89 |
| 4,278,662 | 7/1981 | Löbmann | 424/89 |
| 4,318,903 | 3/1982 | Löbmann | 424/89 |
| 4,338,296 | 7/1982 | Löbmann | 424/89 |

OTHER PUBLICATIONS

Berry, E. S. et al., Journal of Fish Diseases 6(6):501-510 (1983), cited in Biosis Abstract 84:247368.

Shea, T. B. et al., Applied Environmental Microbiology 47(2):250-252 (1984), cited in Biosis Abstract 84:271531.

Computer printout from a background search. The titles and abstracts are considered self-explanatory.

Abstract No. 83 from the 34th Annual Meeting of the Tissue Culture Association held Jun. 12-16, 1983. This discloses a new continuous cell line from goldfish. Journal of the Tissue Culture Assoc. 19(3):255 (1983).

Abstract No. 92 from the 34th Annual Meeting of the Tissue Culture Association held Jun. 12-16, 1983. This discloses a serum-free medium for fish cell cultures. Journal of the Tissue Culture Assoc. 19(3), 257 (1983).

Winton et al, Isolation of a New Reovirus from Chum Salmon in Japan, Fish Pathology, 15, 155-162 (1981). This reference deals with isolation of a fish virus from salmon.

Abstract from the Annual Meeting of the American Society of Microbiology, 1975, Growth of Human Polio Virus Type I in Fish cells, by Sinclair, et al. The title is self-explanatory. p. 210, abstract Q36.

K. B. Tan, Enhancement of simian virus 40 uptake by permissive, semipermissive and non-permissive cells, published in Cytobios, 20, 143-149 (1978?). This reference deals with a monkey virus.

Migus and Dobos, Effect of Ribavirin on the Replication of Infectious Pancreatic Necrosis Virus in Fish Cell Cultures, J. Gen. Virol., 47, 47-57 (1980). This deals with a fish virus.

Meyers, A Reo-like Virus Isolated from Juvenile American Oysters, J. Gen. Virol., 43, 203-212 (1979). This deals with a virus from oysters.

Wharton, Ellender, Middlebrooks, and Stocks, Fish Cell Culture: Characteristics of a Cell Line from the Silver Perch, In Vitro, 13, 389-397 (1977). This reference deals with a cell line from Perch.

Middlebrooks, Ellender, and Wharton, In Vitro, 15, 109-111 (1979). This deals with a cell line from the spotted weakfish.

Berry, Shea and Gabliks, Two Iridovirus Isolates from *Carassium Auratus*, J. Fish Diseases, 6, 501-510 (1983). This deals with the isolation of two viruses from goldfish.

Berry, Goldfish Virus-1: Characterization, Relationship to Goldfish Virus-2, & the Effects of Temperature & Host Cell on In Vitro Pathogenesis. This is a dissertation submitted in partial fulfillment of the requirements for Dr. of Philosophy degree in Biology at Northwestern Univ. (1983), and deals with 2 goldfish viruses.

*Primary Examiner*—Margaret Moskowitz
*Attorney, Agent, or Firm*—Weingarten, Schurgin, Gagnebin & Hayes

[57] ABSTRACT

A method for preparing vaccines against influenza-A, and vaccines prepared thereby. Influenza-A virus is subjected to at least two passages in goldfish cell cultures, resulting in attenuated virus having reduced infectivity and somewhat altered antigenic characteristics relative to the starting virus, but which when used as a vaccine to innoculate mammalian species confers immunity. Immunization tests conducted in mice showed the vaccine to be effective.

3 Claims, 2 Drawing Sheets

INFLUENZA-A VIRUS VACCINE FROM FISH CELL CULTURES

BACKGROUND OF INVENTION

At the present time the use of inactivated influenza A virus vaccine is not fully satisfactory. Development of live attenuated influenza A virus vaccines promises to have significant advantages in that respiratory infections with such attenuated viruses will stimulate more effective and durable immunity than that which occurs with parenteral inactivated vaccines. Recently temperature sensitive (ts) mutants of influenza A virus have been developed and evaluated for level of attenuation and immunogenicity in humans. (Tolpin M. D., M. L. Clements, M. M. Levine, R. E. Black, A. J. Saah, W. C. Anthony, L. Cisneros, R. M. Chanock and B. R. Murphy. 1982. Evaluation of a phenotypic revertant of the A/Alaska/77-ts-1A2 reassortant virus in hamsters and in seronegative adult volunteers: Further evidence that the temperature-sensitive phenotype is responsible for attenuation of ts-1A2 reassortant viruses. *Infection* and *Immunity* 36: 645–650.) Although some strains afford protection, the clinical studies also indicate illness and shedding of the virus from the vaccinated volunteers. (Cate, T. R. and Couch, R. B. 1982. Live influenza A/Victoria/75 (H3N2) virus vaccines: Reactogenicity, immunogenicity, and protection against wild-type virus challenge. *Infection* and *Immunity* 38: 141–146.) Recent reports also indicate that some of the temperature sensitive reassortment viruses (A/Udorn/72-ts-1A2 and A/Alaska/77-ts1A2) undergo progressive loss of temperature sensitivity (Murphy, B. R., L. J. Markoff, N. T. Hosier, J. G. Massicot and R. M. Chanock. 1982. Production and level of genetic stability of an influenza A virus temperature-sensitive mutant containing two genes with ts mutations. *Infection* and *Immunity* 37: 235–242. and Tolpin et al. supra) The loss of the ts phenotype is accompanied by the restoration of virulence.

One object of this invention is to provide a virus vaccine which is more effective and durable than previously described vaccines.

Other objects and advantages of this invention will be apparent from the description and claims which follow taken together with the appended tables and charts.

SUMMARY OF INVENTION

This invention comprises generally new cell cultures in which passage of a virus, such as influenza A virus, indicate viral attenuation, and viral vaccines made by such passage. The cell cultures are derived from aquatic vertebrates such as goldfish. Passages of the virus in these cell cultures results in the production of virions and/or virus associated antigens which when used as vaccines in mammals confer protective immunity against the infections with the wild-type virus. The passage of viruses which replicate at 37° C. replicate in a culture maintained at less than 37° C. This permits selection of mutants which replicate at a sub-body temperature.

DRAWINGS AND TABLES

Figure 2:
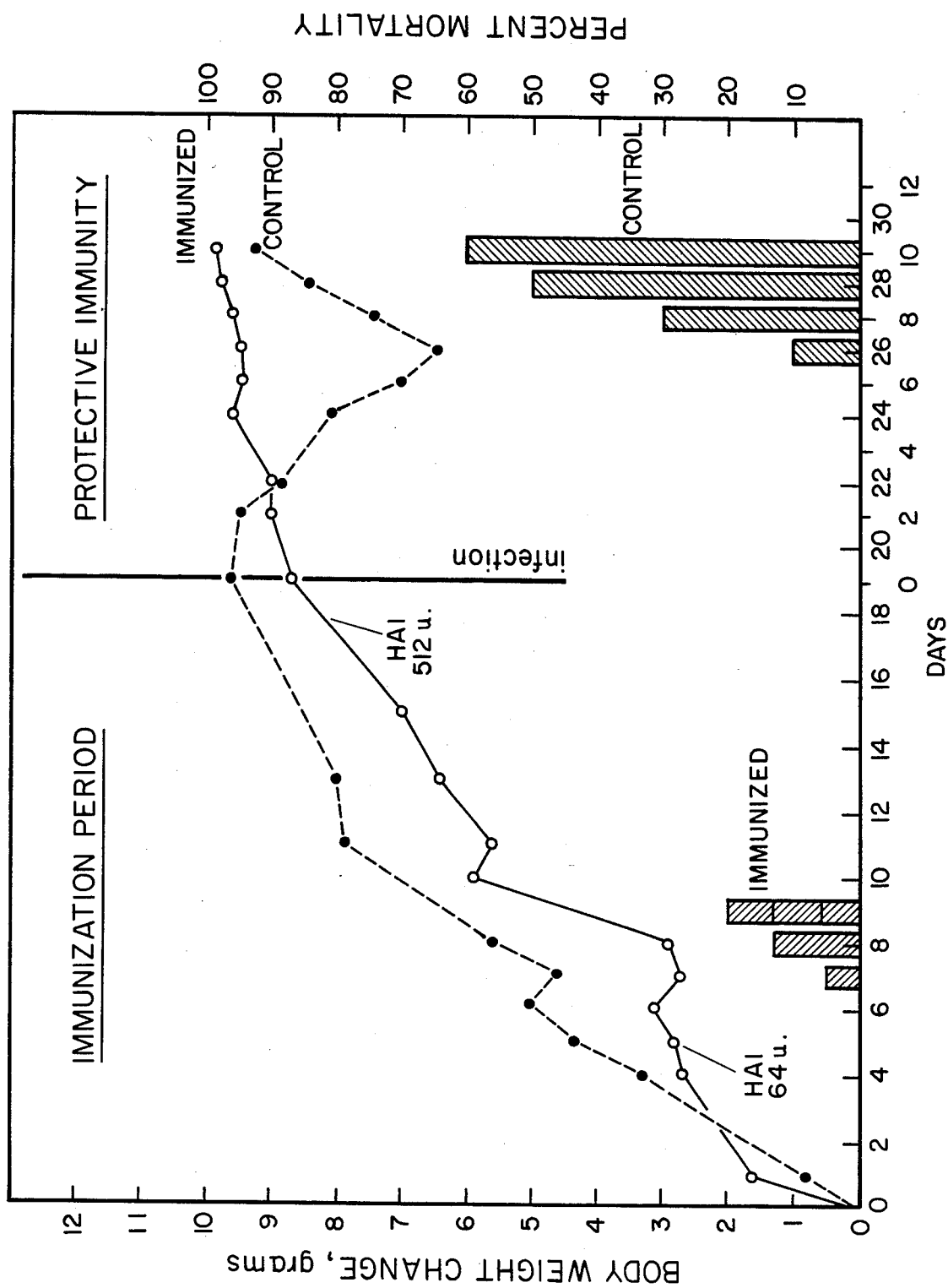

FIG. 1 and FIG. 2 and Tables 1 and 2 show immunity achieved with examples of this invention.

EXPERIMENTAL PROCEDURES

1. Virus

Virus Influenza A/PR-8/34 ($N_1H_1$) strain used in this study was maintained by regular passages in mice and in embryonating chicken eggs. Mice, CD-1 strain, were infected under ether anesthesia with 10 $LD_{50}$ mouse doses (0.05 ml/mouse) intranasally (IN). On the 3rd day post infection the infected lungs were removed, homogenized in Hanks balanced salt solution (HBSS) and the preparation (10% w/v) stored at −60° C. the influenza egg stock preparation was made by infecting 10-day old embryonating eggs (1-16B0 with 10 $ID_{50}$ egg doses (0.5 ml/egg) via the chorioallantoic cavity. The allantoic fluid was harvested on the 3rd day post infection and also stored at −60° ⓒC. The viral infectivity of these mouse and egg stock pools was measured by their titration in mice or eggs respectively and the titers expressed as the $LD_{50}$ or $ID_{50}$ doses.

2. Preparation of Primary Fish Cell Cultures

Primary monolayer cultures from goldfish (*Carassius auratus*), largemouth bass (*Micropterus salmoides*) and yellow perch *Perca flavescens*) were prepared by cell dispersion-trypsinization or by tissue fragment explantation. The cells were grown in two types of growth media: Medium 199 (M-199) or Eagle's Basal Medium (EBM) with Hanks' balanced salt solution (HBSS) supplemented with 15% fetal calf serum and antibiotic mixture (Penicillin 100 u/ml, Streptomycin 100 ug/ml and Fungizone 0.25 ug/ml). In the initial cultures the concentration of $NaHCO_3$ was reduced to $\frac{1}{4}$ or $\frac{1}{2}$ of the concentration normally used in HBSS. All media and its ingredients were from GIBCO Co.

TABLE 1

Immunization of Mice

| VACCINE | TEST PARAMETERS | DAYS | | | | | | | | | | | | Dead/Total |
|---|---|---|---|---|---|---|---|---|---|---|---|---|---|---|
| | | 0 | 1 | 2 | 4 | 5 | 6 | 7 | 8 | 9 | 13 | 14 | 16 | 17 | |
| Control G-cells | Body weights, g | 20.1 | 20.5 | 21.0 | 22.2 | 22.4 | 22.7 | 23.1 | 23.2 | 24.0 | 24.6 | 23.8 | — | 26.0 | |
| | Body wt. change, g | | +0.4 | +0.9 | +2.1 | +2.3 | +2.5 | +3.0 | +3.1 | +3.9 | +4.5 | +3.7 | — | +5.9 | |
| | Body wt. change, % | | +2.0 | +4.5 | +10.5 | +11.4 | +13.0 | +15.0 | +15.4 | +19.4 | +22.4 | +18.4 | — | +29.3 | |
| | Mortality | 0 | 0 | 0 | 0 | 0 | 0 | 0 | 0 | 0 | 0 | 0 | 0 | 0 | 0/10 |
| | Serum HAI units | | | | | | | | | | | | 16 | | |
| 23-4Y | Body weights, g | 22.7 | 21.1 | 22.0 | 22.3 | 23.5 | 23.1 | 24.0 | 24.4 | 24.4 | 24.4 | 25.7 | — | 26.1 | |
| | Body wt. change, g | | −1.6 | −0.7 | +0.6 | +0.8 | +0.4 | +1.3 | +1.7 | +1.7 | +2.7 | +3.0 | — | +3.4 | |
| | Body wt. change, % | | −7.0 | −3.1 | +2.6 | +3.5 | +1.8 | +5.7 | +7.5 | +7.5 | +12.0 | +13.2 | — | +14.9 | |

TABLE 1-continued

|  |  |  |  |  |  |  |  |  |  |  |  |  |  |
|---|---|---|---|---|---|---|---|---|---|---|---|---|---|
| Mortality | 0 | 0 | 0 | 0 | 0 | 0 | 0 | 1 | 0 | 0 | 0 | 0 | 1/20 |
| Serum HAI units |  |  |  |  |  |  |  |  |  | 1024 |  |  |  |

| | | Protective Immunity Against Influenza Virus Infection | | | | | | | | | |
|---|---|---|---|---|---|---|---|---|---|---|---|
| VAC-CINE | TEST PARA-METERS | DAYS | | | | | | | | | Dead/Total |
| | | 17 / 0 | 19 / 2 | 21 / 4 | 22 / 5 | 23 / 6 | 24 / 7 | 25 / 8 | 26 / 9 | 29 / 12 | |
| Control G-cells | Body weights, g | 26.0 | 25.5 | 23.4 | 21.8 | 20.3 | 18.0 | | | | |
| | Body wt. change, g | | −0.5 | −2.6 | −4.2 | −5.7 | −8.0 | | | | |
| | Body wt. change, % | | −2.0 | −10.0 | −16.2 | −22.0 | −30.8 | | | | |
| | Mortality | | | | | 4 | 2 | 2 | 2 | | 10/10 |
| 23-4Y | Body weights, g | 26.1 | 26.2 | 26.6 | 26.2 | 25.6 | 26.0 | | 27.0 | 28.2 | |
| | Body wt. change, g | | +0.1 | +0.5 | +0.1 | −0.5 | −0.1 | | +0.9 | +2.1 | |
| | Body wt. change, % | | +0.4 | +0.5 | +0.4 | −2.0 | −0.4 | | +3.4 | +8.0 | |
| | Mortality | | 0 | 0 | 0 | 0 | 0 | | 0 | 0 | 0/14 |

TABLE 2

| | | Immunization of Mice | | | | | | | | | | | | |
|---|---|---|---|---|---|---|---|---|---|---|---|---|---|---|
| VAC-CINE | TEST PARAMETERS | DAYS | | | | | | | | | | | | Dead/Total |
| | | 0 | 1 | 4 | 5 | 6 | 7 | 8 | 9 | 11 | 13 | 15 | 18 | 19 | |
| Control CAR cells | Body weights, g | 17.5 | 18.3 | 21.8 | 21.9 | 22.5 | 22.1 | 23.1 | | 25.4 | 25.5 | 25.3 | — | 27.1 | |
| | Body wt. change, g | | +0.8 | +4.3 | +4.4 | +5.0 | +4.6 | +5.6 | | +7.9 | +8.0 | +7.8 | — | +9.6 | |
| | Body wt. change, % | | 4.9 | 24.6 | 25.1 | 28.5 | 26.6 | 32.0 | | 45.5 | 45.7 | 44.6 | — | 54.8 | |
| | Mortality | | | | | | | | | | | | | | 0/15 |
| | Serum HAI units | | | | | 0 | | | | | | | | | |
| 23-4C | Body weights, g | 17.5 | 19.1 | 20.2 | 20.3 | 20.6 | 20.3 | 20.4 | | 23.4 | 23.9 | 24.5 | — | 26.2 | |
| | Body wt. change, g | | +1.6 | +2.7 | +2.8 | +3.1 | +2.8 | +2.9 | | +5.9 | +6.4 | +7.0 | — | +8.7 | |
| | Body wt. change, % | | 9.1 | 15.4 | 16.0 | 17.7 | 16.0 | 16.5 | | 33.7 | 36.5 | 40.0 | — | 49.7 | |
| | Mortality | | | | | | 1 | 1 | 1 | | | | | | 3/15 |
| | Serum HAI units | | | | | 64 | | | | | | | | | |

| | | Protective Immunity Against Influenza Virus Infection | | | | | | | | | | |
|---|---|---|---|---|---|---|---|---|---|---|---|---|
| VAC-CINE | TEST | DAYS | | | | | | | | | | Dead/Total |
| | | 19 | 21 | 22 | 24 | 25 | 26 | 27 | 28 | 30 | 33 | 34 | |
| Control CAR cells | Body weights, g | 27.1 | 27.0 | 26.4 | 25.6 | 24.5 | 24.0 | 25.0 | 26.0 | 26.8 | 27.5 | 27.2 | |
| | Body wt. change, g | | −0.1 | −0.7 | −1.5 | −2.6 | −3.1 | −2.1 | −1.1 | −0.3 | +0.4 | +0.1 | |
| | Body wt. change, % | | | −2.6 | −5.5 | −9.6 | −11.4 | −7.7 | −4.1 | −1.0 | +1.5 | +0.4 | |
| | Mortality | | 0 | 0 | 0 | 0 | 1 | 2 | 2 | 1 | 0 | 0 | 6/10 |
| 23-4C | Body weights, g | 26.2 | 26.5 | 26.5 | 27.1 | 27.0 | 27.0 | 27.2 | 27.3 | 27.4 | 28.1 | 28.5 | |
| | Body wt. change, g | | +0.3 | +0.3 | +0.9 | +0.8 | +0.8 | +1.0 | +1.1 | +1.2 | +1.9 | +2.3 | |
| | Body wt. change, % | | +1.2 | +1.2 | +3.4 | +2.7 | +2.7 | +3.8 | +4.2 | +4.6 | +7.3 | +8.8 | |
| | Mortality | | 0 | 0 | 0 | 0 | 0 | 0 | 0 | 0 | 0 | 0 | 0/8 |

3. Explant cultures

Explant cultures were prepared from skin, swimbladder and liver by the method described by Clem, W. L. L. Moewus, and M. Sigel. 1961. Studies with cells from marine fish in tissue cultures. *Proc. Exp. Biol. Med.* 108: 762–766. Skin cultures were prepared from small goldfishes, ranging in size from 3–5 cm. To control microbial contaminants the scaled skin was washed several times with HBSS containing antibiotics (Penicillin, Streptomycin and Fungizone) at 5 times (5X) the prescribed concentration levels. After 20 minutes of exposure to the antibiotics, the skin was peeled away and again soaked for an additional 30 minutes in HBSS containing antibiotics at 2X concentration level. The tissues were then transferred to Petri dishes containing growth medium and minced with scissors to small fragments. After several washings the desired smaller fragments (1 mm or less in size) were selected by sedimentation in the centrifuge tubes. The tissue fragments were then transferred to 25 cm² Falcon flasks containing 1.0 ml volumes of growth medium. After the fragments settle an additional 1.0 ml of the growth medium was added and the cultures then incubated at 25° C. Cultures from swimbladders and livers were prepared by the same procedures.

Cell migration from the explants was evident after four days and monolayers developed within 3 to 4 weeks. Medium changes reflected cell growth rates with initial change conducted by the 10 to 12 day post explanation and thereafter at weekly intervals. Subculturing of the resulting cell monolayers was usually done by rinsing the monolayers with HBSS followed by addition of 1.0 ml of 0.25% trypsin solution. When cells began to detach, the trypsin was carefully drained off, and the cultures incubated for an additional 15 minutes before adding 5.0 ml of the regular growth medium to stop the trypsin action. The cells were then dispersed by vigorous pipetting and the cultures split 1:2, depending on the growth potential of particular cultures.

4. Cell dispersion-trypsinization method

Cultures from swimbladders of goldfish and from other species were prepared by the method described by Kuhn, C. Vielkind, U., and Anders, F. 1979. Cell cultures derived from embryos and melanoma of poeciliid fish. *In Vitro* 15: 537–544. Adult goldfishes, 12–15 cm long, were pinned on a dissecting board, the scales scraped off and the skin washed with 75% ethanol several times, allowing for the ethanol to evaporate each time. The side of the fish was then removed asceptically, the swimbladders removed and soaked for 30 minutes in HBSS with the (2x) antibiotic mixture. The swimbladders were minced in the growth medium, the fragments washed several times and then transferred to a trypsinization flask placed on a magnimixer to agitate the fragments in 0.25% trypsin solution. The trypsin-released cells were collected at 60 minute intervals, cooled in ice bath and the cells harvested by centrifugation at 500 rpm for 15 minutes. Each batch was processed separately.

The trypsinized cells grown at 25° C. resulted in cell monolayers within 10 to 14 days. Subculturing of the cell monolayers was done by the trypinsization procedure. The resulting product is the Gabliks culture.

5. Vaccines

The novel influenza A vaccine preparations were obtained by treatment with two goldfish (*Carassius auratus*) established cell cultures: (1.) the swimbladder Gabliks culture (described above) and (2.) the CAR (CCL-71) cell line obtained from the American Type Culture Collection. Both cell cultures were propagated in Medium 199 (M-199), (Gibco Co.) supplemented with 15% fetal calf (or bovine) serum, glutamine (100 ug/ml), and antibiotic mixture (Penicillin 100 U/ml, Streptomycin 100 ug/ml, and Amphotericin 0.25 ug/ml) incubated at 25° C.

Both the Gabliks and CAR cell monolayer cultures were grown in Falcon flasks and were infected with the above described influenza A egg pool preparations diluted in HBSS. To infect the cells, the growth medium was removed, the cell monolayers washed with HBSS and then inoculated with a virus dilution containing $10^3$ to $10^5$ ID$_{50}$ doses. For viral absorption the cultures were incubated at 37° C. for 60 or 90 minutes, then fed with complete Medium 199 and incubated at 37° C. or 25° C. for periods up to 5 days, depending on the multiplicity of infection.

When the influenza virus infected Gabliks or CAR cell cultures exhibited the virus induced cytopathogenic effects, the cultures were frozen at −60° C. Subsequently, 2nd passage influenza vaccines were prepared by inoculating with the virus/cell suspensions described above in the corresponding Gabliks or CAR cultures and incubating them for periods up to 7 days.

The influenza virus progeny in the culture medium was assayed by their infectivity in embryonated chicken eggs and by hemagglutination tests performed according to the standard procedures (Rovozo and Burke, 1973 A manual of basic virological techniques. Prentice-Hall, Englewood Cliffs, N.J.).

6. Vaccination and Infection of Immunized Mice

A group of 20 female mice (CD-1 strain) were lightly etherized and infected intranasally with the Gabliks attenuated influenza A vaccine and another 20 female mice were infected with the attenuated CAR influenza A vaccine. The procedure was as follows: the frozen cultures were thawed, cells dispersed and disrupted by vigorous shaking and refreezing and then 0.05 ml administered to mice IN. The control groups of 20 female mice received identical preparations of normal noninfected cell culture preparations. Following the immunization, the mice were weighed and observed for possible development of influenza virus induced disease with pathological manifestations. The immune response was assessed by titration of blood serum by the hemagglution inhibition test using 4 hemagglutinating (HA) units. Three weeks after administration of the vaccines, the mice were challenged with the influenza A stock virus infection of 10 or 100 LD$_{50}$ mouse doses. The magnitude of infection was compared by body weight losses and mortality rates.

RESULTS

1. Infection of Fish Cell Cultures

The goldfish (*Carassius Auratus*) Gabliks and CAR cell cultures infected with influenza A/PR-8/34 (H1N1) strain stock dilutions containing $10^3$ to $10^5$ egg ID$_{50}$ or mouse LD$_{50}$ dose levels respectively were incubated at 25°, 32° and 37° C. At these incubation temperatures the cell cultures developed progressive virus induced cytopathogenic effects (CPE) characterized first by enlarged and granulated cells which later tended to shrink, aggregate and detach from the monolayers. The general magnitude of the CPE was related to multiplicity of infection. With large viral doses ($10^5$ ID$_{50}$) cell monolayers were destroyed within 2–3 days, whereas smaller doses ($10^1$ ID$_{50}$) developed CPE only in focal areas. Accordingly, the influenza A virus immunizing preparations were made by infecting 25 cm$^2$ Falcon flask cultures with $10^3$ to $10^4$ egg ID$_{50}$ dose levels and incubating the cultures at 25°, 32° and 37° for 3 to 5 days.

The influenza virus is absorbed rapidly on the fish cell receptors. For example, when an egg pool virus dilution was incubated with Gabliks cells for 90 minutes at 37° C., the HA units in the medium decreased 4-fold. The virus absorbed on these cells was not removed by washing the cell monolayers and results in cell infection with CPE. The viral progeny was evidenced by presence of viral hemagglutinin and infectivity in embryonated eggs. From the comparative results of 7 experiments it was evident that there were at least 2-fold and 4fold increases in HA units indicating that influenza A replicated in this culture.

2. Protective immunity (a) Experiment No. 23-4Y with Gabliks Cell Cultures at 37° C.

1. Vaccine

The Gabliks' cell cultures (10 ml flasks) were infected with influenza A (PR-8/34) egg preparation diluted in HBSS=$6 \times 10^3$ ID$_{50}$ units per culture. After the absorption period of 90 minutes at 37° C., the virus dilution was removed and the cultures incubated with the regular growth medium (M-199) at 37° C. On the 2nd day post infection, the cells exhibited a marked cytopathogenic effect (CPE)=4+ reaction (75% of the cells exhibited CPE). The cultures were frozen and subsequently used to infect new Gabliks cell cultures (5 ml flasks) with 1.0 ml of the first passage viral progeny by applying the same procedures. The second passage cultures exhibited only the focal CPE=1+ reaction (25% of the cells were affected). On the 5th day the cultures were frozen and then used for vaccination of mice.

2. Immunization of Mice

Twenty female mice CD-1 strain were vaccinated with 0.05 ml of undiluted second passage preparation administered intranasally. Possible development of illness induced by the vaccine was assessed by body weight changes. The results on body weight changes presented in Table 1 and FIG. 1 show progressive body weight gains during the immunization period with a slight inhibitory effect during the period from day 6 to day 8. On day 8 post vaccination the body weights increased 1.3% in comparison to a 5.7% weight gain in the control group mice. On day 17, the weight gains were 11.5% and 18.9% respectively.

Following the vaccination all mice appeared normal without any detectable signs of illness. Serum antibody levels in blood pooled from 5 mice were measured by the influenza hemagglutination inhibition test. On day 16 post vaccination the HAI titer was 1024 units, whereas in the control mice the influenza antibodies were not detected.

3. Results of Infection

On day 17 post vaccination the mice were infected with 100 $LD_{50}$ mouse units of influenza virus. The normal-non-vaccinated mice developed a rapidly progressing disease with body weight losses evident on day 2 post infection. By day 7 these mice had lost 25% of their body weights recorded at the time of infection and all of the control animals died by the 9th day. (Table 1, FIG. 1). The vaccinated mice did not show any signs of disease and all of them survived the infection with (100 $LD_{50}$) influenza virus.

(b). Experiment No. 23-4C (CAR cell)

1. Vaccine

CAR cell cultures were infected with the same influenza A virus preparation by applying the procedures described for experiment No. 23-4Y. The cytopathogenic effect in the CAR cell cultures was comparable to the effects observed in the Gabliks cell culture.

2. Immunization

Vaccination of mice was also performed by the procedures described for experiment No. 23-4Y. The results summarized in Table 2 and FIG. 2 showed an inhibition of growth of the vaccinated mice during the period from day 4 to day 8, when also 3 mice (3/15) died. On day 8 the immunized mice had gained 2.9% of their original body weights in comparison to a 5.6% weight gain in the control group animals. The serum antibody HAI titers of influenza virus increased: on day 5 it was 64 HAI units and on day 18, 512 HAI units.

3. Results of Infection

On day 19 post vaccination the mice were infected with influenza virus, 10 $LD_{50}$ mouse units. The non-vaccinated mice showed body weight losses evident on day 3 post infection and by the 7th day the mice had lost 11.4% of their body weights. The illness was progressing and resulted in a 60% mortality in the non-vaccinated mice whereas all of the vaccinated mice continued to grow without observable signs of illness with no mortality. (Table 2, FIG. 2)

I claim:

1. A method for preparing an attenuated influenza-A virus vaccine for the immunization of mammals, comprising passaging said influenza-A virus at least two times in a goldfish cell culture.

2. The method of claim 1 wherein the cell culture is a culture of the goldfish CAR (CCL-71) cell line.

3. The method of claim 1 wherein the cell culture is prepared from the swimbladder of a goldfish.

* * * *

UNITED STATES PATENT AND TRADEMARK OFFICE
CERTIFICATE OF CORRECTION

PATENT NO. : 4,783,411
DATED : November 8, 1988
INVENTOR(S) : Janis Gabliks

It is certified that error appears in the above-identified patent and that said Letters Patent is hereby corrected as shown below:

Column 2, line 26, "C. the" should read --C. The--

Column 2, line 31, "-60° © C." should read ---60° C.--

Column 2, line 44, "and antibiotic" should read --and an antibiotic--

Columns 3 & 4, Table 2, 2nd section, after column headings at line 37 beginning with "VAC-" and "TEST", insert

| CINE | PARAMETERS | 0 | 2 | 3 | 5 | 6 | 7 | 8 | 9 | 10 | 13 | 14 | Total |
|---|---|---|---|---|---|---|---|---|---|---|---|---|---|

Column 5, line 19, "trypinsization" should read --trypsinization--

Column 5, line 55, "(Rovozo" should read --(Rovozzo--

Column 6, line 43, "4fold" should read --4-fold--

Signed and Sealed this

Nineteenth Day of December, 1989

Attest:

JEFFREY M. SAMUELS

*Attesting Officer*   *Acting Commissioner of Patents and Trademarks*